(12) United States Patent
Schumacher

(10) Patent No.: US 6,440,451 B1
(45) Date of Patent: Aug. 27, 2002

(54) USE OF CRATAEGUS FORMULATIONS FOR PROPHYLAXIS AND TREATMENT OF NEOPLASTIC DISEASES

(75) Inventor: Katrin U. Schumacher, Aachen (DE)

(73) Assignee: Nativia Health Products GmbH, Innsbruck (AT)

( * ) Notice: Subject to any disclaimer, the term of this patent is extended or adjusted under 35 U.S.C. 154(b) by 0 days.

(21) Appl. No.: 09/700,174
(22) PCT Filed: May 14, 1999
(86) PCT No.: PCT/EP99/03302
§ 371 (c)(1), (2), (4) Date: Nov. 13, 2000
(87) PCT Pub. No.: WO99/59605
PCT Pub. Date: Nov. 25, 1999

(30) Foreign Application Priority Data

May 20, 1998 (DE) .......................................... 198 23 679

(51) Int. Cl.⁷ .......................... A61K 47/00; A61K 35/78
(52) U.S. Cl. ....................................... 424/439; 424/725
(58) Field of Search ................................. 424/439, 725

(56) References Cited

FOREIGN PATENT DOCUMENTS

| JP | JO 4005-237 A | 4/1990 |
| WO | WO 98/41096 | 9/1998 |

OTHER PUBLICATIONS

Fotsis et al, "Flavonoids, Dietary–derived Inhibitors of Cell Proliferation and in Vitro Angiogenesis", Cancer Research 57.2916–2921, Jul. 15, 1997.

Saenz et al, "Extracts from Viscum and Crataegus are Cytotoxic against Larynx Cancer Cells", 1997 Verlag der Zeitschrift fur Naturforschung, 0939–5075/97/0100–0042.

Patent abstracts of Japan vol. 014, No. 146 (C–0704), (Mar. 1990) & Jp 02 017121 A (Taiyo Kagaku Co Ltd), (Jan. 1990) abstract.

Ali H. Alwan et al.: "Effects of Plant Extracts on ARYL Hydrocarbon Hydroxylase Activity and 3H–Benzo (A9Pyrene Binding to DNA." Journal of Food Safety., vol. 10, No. 3, 1990, pp. 209–218.

Kyung–Seop Ahn et al.: "Corosolic Acid Isolated from the Fruit of *Crataegus Pinnatifida*VAR. Psilosa is a Protein Kinase C Inhibitor as Well as a Cytotoxic Agent." Planta Medica, vol. 64, No. 5, 1998, pp. 468–470.

M.T. Saenz et al.: "Extracts from Viscum and Crataegus are Cytotoxic Against Larynx Cancer Cells." Zeitschrift Fuer Naturforschung. § C. Biosciences., vol. 52, No. 1–2, (Jan. 1997–Feb. 1997) pp. 42–44.

Ahn et al. "corosolic Acid Isolation from the fruit of *Crataegus pinnatifida* var. Psilosa is a Protein Kinase C Inhibitor as well as Cytotoxic Agent." Planta Medica, vol. 64, No. 5, pp. 468–470 (1998).*

* cited by examiner

Primary Examiner—Thurman K. Page
Assistant Examiner—Blessing Fubara
(74) Attorney, Agent, or Firm—Nixon & Vanderhye P.C.

(57) ABSTRACT

The present invention relates to the use of formulations from Crataegus for the preparation of pharmaceutical preparations or food supplements for the prophylaxis and/or treatment of tumour diseases, the formulations substantially comprising constituents of Crataegus which are soluble in polar solvents. The invention furthermore relates to the use of Crataegus plant parts for the preparation or infusions. Compositions for the prophylaxis and/or treatment of tumour diseases are furthermore included.

22 Claims, No Drawings

USE OF CRATAEGUS FORMULATIONS FOR PROPHYLAXIS AND TREATMENT OF NEOPLASTIC DISEASES

The present invention relates to the use of formulations from Crataegus for the preparation of pharmaceutical preparations or food supplements for the prophylaxis and/or treatment of tumour diseases, the formulations substantially comprising constituents of Crataegus which are soluble in polar solvents. The invention furthermore relates to the use of Crataegus plant parts for the preparation of infusions. Compositions for the prophylaxis and/or treatment of tumour diseases are furthermore included.

In spite of advances in modern medicine, tumour diseases, i.e. malignant neoformations, still count among the most frequent diseases with in most cases very poor courses of the disease and predominantly fatal consequences. Undesirable side effects narrow the use of currently available medicaments in prophylaxis and treatment. A large number of active chemotherapeutics (cytostatics and cytotoxics), such as e.g. 5-fluorouracil or methotrexate, have so far been developed. However, the disadvantage of chemotherapeutics lies in the potent side effects. The side effects are to be attributed to the fact, inter alia, that the active compounds employed in chemotherapy also have a cytostatic and/or cytotoxic action on "healthy" cells, i.e. cells which proliferate normally. This leads in particular to damage to cells which normally divide frequently, such as e.g. keratinocytes, fibroblasts, endothelial and epithelial cells, stem cells of blood formation (haematopoietic system) and gametes, with the consequence of undesirable actions, such as e.g. hair loss (alopecia), damage to mucous membranes (mucositis, intestinal ulcerations), suppression of blood formation (myelosuppression with the consequence of anaemia, infections and bleeding complications) and infertility. This limits the applicability of the currently available chemotherapeutics in treatment and prohibits their use in prophylaxis of neoplastic diseases.

The object of the present invention is therefore to provide a composition, in particular a pharmaceutical preparation or food supplement, for the prophylaxis and/or treatment of tumour diseases which does not have the side effects mentioned for the chemotherapeutics known in the prior art. In particular, an object of the present invention is to provide a composition which, in contrast to the chemotherapeutics currently used, has no effect or only a mild cytostatic or cytotoxic effect on normally proliferating cells.

The object is achieved according to the invention in that a formulation from Crataegus which substantially comprises constituents of Crataegus which are soluble in polar solvents (including polar protic solvents) is used for the preparation of a composition for the prophylaxis and/or treatment of tumour diseases (neoplastic diseases).

Formulations which substantially comprise constituents which are soluble in polar solvents are therefore to be understood as meaning those formulations which are obtainable employing processes with which polar constituents of Crataegus are obtained. The possible processes for the preparation of these formulations here are mentioned below by way of example. The term "polar solvents" in the context of the invention is generally understood as meaning aqueous and non-aqueous solvents, the latter group including, in particular, organic nitrogen and oxygen compounds, but not carbon disulphide, carbon tetrachloride and saturated hydrocarbons.

In the context of the present invention, the composition can be pharmaceutical preparations, medicaments, remedies, food supplements, dietary supplements, botanics, herbal remedies, additives to food supplements or to foodstuffs and the like, such as nutritive additives, teas or the like, in particular depending on the specification according to medical preparations law.

According to the invention, it has been found, surprisingly, that formulations which substantially comprise constituents of Crataegus which are soluble in polar solvents are particularly suitable for the prophylaxis and/or treatment of tumour diseases without showing the undesirable side effects of the chemotherapeutics known from the prior art.

Crataegus extracts have already been employed in folk medicine for a long time for the treatment of cardiovascular diseases, and have since also been recognized by science as effective for these diseases.

Crataegus is widespread throughout the world in the temperate climate zones on the northern and southern hemispheres and in the high mountains of the tropics (R. Kaul, "Der Weißdorn: Botanik, Inhaltsstoffe, Qualitätskontrolle, Pharmakologie, Toxikologie und Klinik [The Hawthorn: Botany, constituents, quality control, pharmacology, toxicology and clinical aspects]", 1st edition, Wissenschaftliche Verlagsgesellschaft, Stuttgart 1998). It is the largest genus of the Maloideae (Pomoideae) a sub-family of the Rosaceae. The genus Crataegus includes approx. 100 to 200 true species (I. Bauer and U. Hoelscher, "Crataegus" in R. Hansel, K. Keller, H. Rimpler, G. Schneider (editors), Hagers Handbuch der Pharmazeutischen Praxis [Hagers handbook of pharmaceutical practice], volume 4, 5th edition, Springer verlag, Berlin 1992, 1040–1062). In Central Europe, *Crataegus laevigata* (synonym: *Crataegus oxyacantha*) and *Crataegus monogyna* and hybrids thereof are chiefly encountered; these are also the predominant Crataegus species in the western Mediterranean region and North Africa, while in the eastern Mediterranean region and Eurasia *Crataegus pentagyna* and *Crataegus nigra* are the preferred species, and in the eastern part of Eurasia, in addition to *C. laevigata* and *C. monogyna, C. curvisepala* and *C. azarolus* also grow. *C. cuneata* and *C. pinnatifida* are employed medicinally in Japan, China and adjacent regions, while in North America *C. berberifolia, C. aestivalis, C. chrysocarpa, C. crus-galli* and *C. pruinosa* are also taken for cardiovascular symptoms, at least in folk medicine. Most studies of the constituents carried out on *C. laevigata* have shown that all the plant parts of Crataegus contain a large number of constituents from the most diverse groups of substances (cf. F. Hoffmann, Pharmaceutica Acta Helvetiae 36 (1961) 30–39; B. Lay "Zur Chromatographie von Pimpinella major, Panax Ginseng, *Crataegus oxyacantha, Tussilago farfara* und *Mentha piperita* [The chromatography of Pipinella major, *Panax ginseng, Crataegus oxyacantha, Tussilago farfara* and *Mentha piperita*]", dissertation 1965, Ludwig-Maximilians University Munich; N. Nikolov et al., "Recent investigations of Crataegus flavonoids" in L. Farkas, M. Gábor, F. Kállay, H. Wagner (editors), Elsevier Scientific Publishing Company, Amsterdam 1982, 325–344; M. Schüssler, "In-vitro-Untersuchungen zur Pharmakologie von Flavonoiden aus den offizinellen Crataegus Spezies und ihre analytische Charakterisierung [In vitro studies of the pharmacology of flavonoids from the officinal Crataegus species and their characterization by analysis]", dissertation 1995, Philipps-University Marburg; R. Kaul, "Der Weißdorn [The Hawthorn]", loc. cit.).

Crataegus has a distinct cardiovascular action. The numerous studies are summarized in detail by Ammon et al. (H. P. T. Ammon et al., "Crataegus, Toxikologie und Pharmakologie, Teil I: Toxizität [Crataegus, toxicology and pharmacology, part I: Toxicity]", Planta medica 43 (1981) 105–120; H. P. T. Ammon et al., "Crataegus, Toxikologie und Pharmakologie, Teil II: Pharmakodynamik [Crataegus, toxicology and pharmacology, part II: Pharmacodynamics]", Planta medica 43 (1981) 209–239; H. P. T. Ammon et al., "Crataegus, Toxikologie und Pharmakologie, Teil III: Pharmakodynamik und Pharmakokinetik [Crataegus, toxicology and pharmacology, part III: Pharmacodynamics and pharmacokinetics]", Planta medica 43 (1981) 313–322; the works of Ammon et al. have also served as a basis for the monograph in Bundesanzeiger [German Federal Gazette] no. 1 of Mar. 1, 1984, amended in Bundesanzeiger [German Federal Gazette] no. 85 of May 5, 1988 and revised by the monograph in Bundesanzeiger [German Federal Gazette] p. 7360 of Jul. 19, 1994 "Crataegi flos (hawthorn blossom), Crataegi folium (hawthorn leaves), Crataegi folium cum flore (hawthorn leaves with blossom), Crataegi fructus (hawthorn fruit)"). The approval of the drug attests positively inotropic, chronotropic, dromotropic and negatively bathmotropic properties and an increase in coronary and myocardial circulation for Crataegus. Indications are mild formsart failure and of cardiac arrhythmia.

The antiproliferative properties of individual flavonoids, from which quercetin and luteolin-7-glucoside are also found in Crataegus in smallest amounts, were investigated in a work by Fotsis et al. (Cancer Research 57 (1997) 2916–2921). It was found that quercetin and luteolin-7-glucoside have an inhibiting effect on the proliferation of human neuroblastoma and breast carcinoma cells. However, at the same time it was also found that, like other chemotherapeutics already known, it also inhibits the proliferation of human fibroblasts, keratinocytes and endothelial cells, i.e. that is to say physiologically proliferating cells which occur naturally in the human and animal organism. The particular half-maximum concentrations required in each case for inhibition here were in the same range for the tumour cells and the physiological cells. This means that the use of flavonoids as individual substances in active concentrations has the same undesirable effects as have been mentioned above for all known chemotherapeutics.

In the context of the present invention, it has now been found, surprisingly, that formulations of Crataegus which substantially comprise constituents (i.e. mixtures of constituents) of above-ground (aerial) Crataegus plant parts which are soluble in polar solvents have a cytostatic and/or cytotoxic action against tumour cells but do not show the antiproliferative action observed for the individual substances described, i.e. isolated flavonoids, on physiologically dividing cells (and the resulting undesirable side effects, monograph in Bundesanzeiger [German Federal Gazette] p. 7360 of Jul. 19, 1994). In particular, long-term, high-dosed administration of such Crataegus formulations also does not lead to damage of cells which physiologically divide frequently, such as, in particular, e.g. keratinocytes, fibroblasts, endothelial and epithelial cells, stem cells of blood formation (haematopoietic system) and gametes (I. Bauer and U. Hoelscher, "Crataegus", loc. cit.).

Cytotoxic effects of hexane extracts from Crataegus and of triterpene-enriched fractions obtained therefrom have been described in works by Saenz et al. (Zeitschrift für Naturforschung 52c (1997) 42–44). The authors attributed the cytotoxic action to triterpene compounds.

As has been shown in the context of the present invention, the formulations from Crataegus used according to the invention surprisingly have a broader action spectrum than hexane extracts. While hydrophobic hexane extracts show no or only a mild cytotoxic action against a large number of various tumour cell lines, the formulations which substantially comprise constituents which are soluble in polar solvents have a cytostatic and/or cytotoxic action against all the tumour cell lines investigated, the inhibition of cell proliferation being significantly more pronounced in the formulations of the present invention.

In the context of the present invention, all Crataegus species, in particular those mentioned above, are possible for the preparation of pharmaceutical preparations or of food supplements, it being possible for all the above-ground (aerial) plant parts, in particular leaves (folii), blossom (flores), fruit (fructus) and mixtures thereof (e.g. folium cum flores), to be used.

The formulations can be prepared by all the processes known to the expert which are employed for the preparation of phytopharmaceuticals, such as e.g. pressing (pressed juice), maceration, agitation maceration, shaking maceration, digestion, agitation digestion, (exhaustive) percolation, Soxhlet extraction, evacolation, recolation, fluidized extraction, Ultra-Turrax extraction, ultrasonic extraction, processes with concentration of first runnings and/or after-runnings, counter-current processes and also more recent processes, such as e.g. extraction with liquids or supercritical liquids or gases, without or with subsequent purification, such as e.g. by filtration, decanting, sedimentation, centrifugation, adsorption, precipitation, chromatography etc. (cf. e.g.: J. Ploschke, "Extraktion [Extraction]" in E. Nürnberg, P. Surmann (editors), Hagers Handbuch der Pharmazeutischen Praxis [Hagers handbook of pharmaceutical practice], volume 2, 5th edition, Springer Verlag, Berlin 1991, 403–411; J. Ziegenmeyer, "Zubereitungen aus Pflanzen und Drogen [Formulations from plants and drugs]" in E. Nürnberg, P. Surmann (editors), Hagers Handbuch der Pharmazeutischen Praxis [Hagers handbook of pharmaceutical practice], volume 2, 5th edition, Springer Verlag, Berlin 1991, 1015–1032; R. Voigt, "Durch Drogenextraktion gewonnene Arzneiformen [Medicament forms obtained by drug extraction]" in Pharmazeutische Technologie [Pharmaceutical technology], 8th edition, Ullstein Mosby Verlag, Berlin 1995, 525–552); monograph "Weißdornfluidextrakt [Hawthorn fluid extract]" Deutsches Arzneibuch [German Pharmacopoeia] 10 (DAB 10), 2nd supplement of 1993, official edition, Deutscher Apotheker Verlag, Stuttgart; monograph "Crataegi Extractum Siccum Normatum" of Pharmacopoeia Helvetica [Swiss Pharmacopoeia] VII). In the context of the present invention, these preparation processes can be carried out both on a larger "industrial" scale, i.e. e.g. by a manufacturer of medicaments, and in the context of individual formulations, e.g. by the pharmacist. The formulation of infusions is also included according to the invention, the abovementioned Crataegus plant parts being employed for this.

According to a particular embodiment of the invention, the Crataegus formulation is an extract obtainable by extraction with water, alcohol, acetic acid, liqueur wine, a supercritical gas, a supercritical liquid or mixtures thereof as the extraction agent.

According to another embodiment of the invention, the formulation is a pressed juice. It has been found that pressed juices of Crataegus which substantially comprise hydrophilic constituents (cf. I. Bauer and U. Hoelscher, "Crataegus" in R. Hänsel, K. Keller, H. Rimpler, G. Schneider (editors), Hagers Handbuch der Pharmazeutischen Praxis [Hagers handbook of pharmaceutical practice], volume 4, 5th edition, Springer Verlag, Berlin 1992, 1040–1062 and J. Ziegenmeyer, "Zubereitungen aus Pflanzen und Drogen

[Formulations from plants and drugs]" in E. Nürnberg, P. Surmann (editors), Hagers Handbuch der Pharmazeutischen Praxis [Hagers handbook of pharmaceutical practice], volume 2, 5th edition, Springer Verlag, Berlin 1991, 1015–1032) are also particularly suitable. Pressed juices are preferably prepared from the above-ground (aerial) plant parts, preferably the fruit.

If pressed juices are used according to the invention, they can either be employed directly as a pharmaceutical preparation or as a food supplement, or can be diluted with liquids or solutions suitable for this purpose, preferably water, aqueous salt solutions, ethanol, syrups or wines (medicinal wines) or mixtures thereof. Further additives familiar to the expert can moreover be added, e.g. for galenical reasons, for preservation, for improving the smell, taste and appearance, for improving the particular pharmacokinetics or pharmacodynamics sought or for other reasons. The pressed juices can also be concentrated by processes known to the expert.

According to a particular embodiment of the invention, the use of extracts obtainable with polar extraction agents, i.e. with extraction agents which transfer substantially polar constituents from Crataegus into the extract, is preferred. In this connection, aqueous and/or alcoholic extracts and extracts prepared with supercritical liquids or gases under conditions which transfer predominantly polar constituents from the plant parts into the extract are particularly preferred. In the context of the present invention, any alcohol which is water-miscible and gives an aqueous solution which leads, as the extraction agent, to the composition of the extracts which is used according to the invention can be employed. In the case of alcoholic extracts, possible extraction agents are, in particular, lower aliphatic alcohols having one to ten, preferably one to six C atoms, in particular alcohols from the group consisting of methanol, ethanol, propanol, butanol, pentanol and/or hexanol, including their isomers and mixtures thereof. The fluid extracts can be obtained from above-ground (aerial) plant parts e.g. with lower alcohols (preferably C1–C6), with water, with aqueous alcoholic solutions, with dilute acetic acid, with liqueur wines or with other extraction agents which transfer polar constituents from the plants into the extract, or can be generated as pressed juice, preferably from fruits.

In addition to water, alcohol(s) and other extraction agents as those which transfer polar constituents from the plants into the extract, the extraction can also be carried out with a mixture of the extraction agents mentioned; a mixture of alcohol and water in particular is the extraction agent, an alcohol/water mixture with a content of 10 to 99 vol. % alcohol being preferred. According to a particularly preferred embodiment of the invention, the extraction agent is an alcohol/water mixture with a content of 15 to 95 vol. % alcohol.

If fluid extracts are used according to the invention, they can be employed either directly as a pharmaceutical preparation or as a food supplement, or be diluted with liquids or solutions suitable for this purpose, preferably water, aqueous salt solutions, ethanol, syrups or wines (medicinal wines) or mixtures thereof. Further additives can moreover be added, e.g. for galenical reasons, for preservation, for improving the smell, taste and appearance, for improving the pharmacokinetics or pharmacodynamics sought or for other reasons. The fluid extracts can also be concentrated by known methods, e.g. to Extractum spissum.

The use of dried extracts which are obtainable by removal (e.g. by evaporation under reduced pressure or other processes familiar to the expert) of the extraction agent (e.g. in the case of fluid extracts) or of the solvent (e.g. in the case of pressed juices) and subsequent drying (such as e.g. by lyophilization, spray drying or other processes familiar to the expert) is furthermore possible in the context of the present invention (cf. J. Ziegenmeyer, "Zubereitungen aus Pflanzen und Drogen [Formulations from plants and drugs]", loc. cit. and R. voigt, "Durch Drogen-extraktion gewonnene Arzneiformen [Medicament forms obtained by drug extraction]", loc. cit.). The removal of the extraction agent or solvent is particularly desirable if it is not suitable as such or is suitable to only a very limited extent for administration to humans or animals. The dried extract can be used as such or subsequently dissolved, emulsified, dispersed or suspended again, if desired, in a suitable medium, in particular in a physiologically tolerated liquid, water, aqueous salt solutions, ethanol, wines (medicinal wines) and other solvents which, in particular, convert the polar constituents of the extracts in to a suitable state in respect of the chosen galenics and from the aspect of the pharmacokinetics, or mixtures of the liquids mentioned, being preferred for preparation of the solution, emulsion, dispersion or suspension. For uptake in ethanol, uptake of the dried extracts in aqueous ethanol having a concentration of 15 to 75 vol. % is preferably suitable.

Suitable additives can be admixed to the dried extract used as such or after preparation of a solution, dispersion, emulsion or suspension, e.g. for dilution or for galenical reasons, for preservation, for improving the smell, taste and appearance, for improving the pharmacokinetics or pharmacodynamics sought or for other reasons.

According to the invention, the formulations mentioned can be prepared either individually or in the form of mixtures or combinations of the formulations mentioned, in particular from the plant parts, fluid extracts, pressed juices, dried extracts etc. mentioned. Extracts which have been obtained with various extraction agents and/or from various plant parts, for example, can be mixed with one another here, such as e.g. an ethanolic dried extract from leaves and blossom dissolved in a pressed juice from fruits.

According to a particular embodiment of the invention, the formulation used is an extract which is obtainable by a process in which plant parts of Crataegus are first extracted with a lipophilic (aprotic) solvent, in particular with an apolar aprotic solvent such as e.g. hexane, heptane or the like, and then, in a further step, either a pressed juice is prepared from the plant parts treated in this way or the plant parts treated in this way are treated with one of the above-mentioned polar extraction agents, in order to substantially transfer the constituents soluble in these solvents from the plants into the extract. In other words, in the context of the present invention, the formulation can be an extract which is obtainable from Crataegus plant parts which have first been subjected to an extraction with a lipophilic (apolar) extraction agent before the extraction with the polar extraction agent, i.e. in a prior step.

The formulations used according to the invention for the prophylaxis and/or treatment of tumour diseases are preferably standardized in respect of their content of active compound, the so-called indicator substances for the presence according to the invention of constituents which dissolve in polar solvents being flavonoids, preferably hyperoside according to Deutsches Arzneibuch [German Pharmacopoeia] 10, basic edition 1991 (DAB 10) "Weißdornblätter mit Blüten [Hawthorn leaves with blossom]" or DAB 10—2nd supplement 1993, "Weißdornfluidextrakt [hawthorn fluid extract]" or vitexin or a mixture of vitexin and hyperoside according to Note Technique Pro Pharmacopoea (NTPP) 708/709 "Extrait d'Aubepine" [Crataegus extract] (sec) or procyanidines as cyanidine chloride according to Deutscher Arzneimittel Codex [German Pharmaceuticals Codex] 86 (DAC 86), 4th supplement 1992, or epicatechin according to the monograph in Bundesanzeiger [German Federal Gazette] p. 7360 of Jul. 19, 1994.

According to a particular embodiment of the invention, the extracts used according to the invention comprise about 0.1 to 13 wt. %, preferably about 0.2 to 6.5 wt. %, and particularly preferably about 0.24 to 4.0 wt. % or 0.24 to 2.0 wt. % flavonoids and/or about 0.05 to 20 wt. %, preferably about 0.1 to 10.0 wt. %, and particularly preferably about 0.2 to 5.0 wt. % procyanidines (for Crataegus leaves and/or blossom determined according to Bundesanzeiger, loc. cit.; according to a particular embodiment, the extracts from Crataegus fruits comprise about 0.05 to 10 wt. %, preferably about 0.1 to 5.0 wt. %, and particularly preferably about 0.2 to 3.0 wt. % procyanidines determined according to DAC 86, loc. cit.).

In the context of the present invention, the formulations are used for the preparation of compositions, in particular pharmaceutical formulations and food supplements, for the prophylaxis and/or treatment of tumour diseases, i.e. malignant or semi-malignant neoplastic diseases and precancerous stages, in humans and in animals.

The formulations are particularly suitable for the prophylaxis and treatment of tumour diseases from the group consisting of precancerous stages, carcinomas, sarcomas (incl. leukaemias and lymphomas), teratomas, blastomas and mixed tumours; and in turn here, in particular colon carcinomas and rectum carcinomas and other neoplastic diseases of the digestive tract, including its appended organs (in particular of the oral cavity, oesophagus, stomach, intestine, liver, gallbladder and pancreas), of kidney carcinomas and other neoplastic diseases of the urogenital system (here in particular of the ovary, cervix, uterus, bladder, prostate and testes), of osteosarcomas and other sarcomas (in particular fibro-, leiomyo-, rhabdomyo- and liposarcomas and leukaemias and lymphomas) and other neoplastic diseases of the supporting apparatus, of melanomas and other neoplastic diseases of the skin, mucous membranes and their appended organs, of glioblastomas and other neoplastic diseases of the central and peripheral nervous system, including its supporting tissue, and of neoplastic diseases of the respiratory tract (here in particular of the larynx, pharynx, bronchi and alveolar cells), of the breast (mamma), thyroid and parathyroid and of mixed tumours.

The use according to the invention of formulations which chiefly or substantially comprise constituents of Crataegus which dissolve in polar solvents have the advantage that substantial undesirable side effects are as yet unknown for them.

Since no serious side effects are so far known for such Crataegus extracts, the dosage is not critical, so that the extracts can also be concentrated, if appropriate.

In the context of the present invention, in general the dosage of the extracts usually used for cardiovascular diseases, that is to say about 0.1 to 1.8 g dried extract/day or 0.5 to 100 g fluid extract/day or about 0.1 to 1 liter tea/day or about 1.0 to 100 g juice/day, can be chosen for the prophylaxis and/or treatment of tumour diseases. However, because of the good tolerability of Crataegus formulations, which has already been demonstrated in the context of treatment of cardiovascular diseases, an increase in the dosage is conceivable.

The present invention furthermore relates to compositions for the prophylaxis and/or treatment of tumour diseases which comprise an abovementioned formulation which substantially comprises constituents of Crataegus which dissolve in polar solvents, the compositions being either pharmaceutical preparations, food supplements, additives to food supplements or additives to foodstuffs. According to a particular embodiment of the invention, these compositions can also be present in a form for the preparation of infusions, e.g. as teas.

On the basis of the cytostatic and cytotoxic effects shown in the context of the present invention, these formulations open up a new therapeutic use. With the use according to the invention of the formulations, it is therefore possible to supplement or replace the treatment measures which have so far not yet been finally satisfactory against (semi-)malignant neoplastic diseases. Because of their exceptionally good tolerability in particullar, it is possible to use the abovementioned Crataegus extracts and pressed juices not only in treatment of these diseases, but also in their primary (that is to say already before the occurrence of a disease) and secondary (that is to say to prevent a recurrence or a second tumour after treatment) prophylaxis.

On the basis of their cytostatic or cytotoxic action on (semi-)malignant neoplastic cells/tumours in humans and animals, the formulations from Crataegus are suitable for use in the primary and secondary prophylaxis and the treatment (adjuvantly, palliatively or under certain circumstances also solely as the essential active substance) of (semi-)malignant neoplastic diseases in humans and animals, formulations also in combination with other phytopharmaceuticals or in combination with chemically defined substances, i.e. e.g. with known chemotherapeutics (cytostatics and/or cytotoxics or other pharmaceuticals) or food supplements or with foodstuffs being possible.

The compositions according to the invention can be formulated for external or internal use. For external use, they can be used transdermally or ocularly for application directly to the tumour. Internal use can be enteral or parenteral. If it is parenteral, it can take place, in particular, by inhalation, by infusion, by subcutaneous or intramuscular or intravenous injection, intravaginally, intrauterinally, rectally, intraurethrally or intravesically and by direct injection into the tumour or the affected tissue or organ. The Crataegus formulations used according to the invention are formulated according to the particular chosen form of administration. Possible medicament forms are therefore e.g. inhalation solutions, aerosols, dusts, mists, instant teas, tea formulations, infusions, decoctions or macerations, as well as foams, mixtures, shaking mixtures, pulverulent forms, powders, tablets, coated tablets, granules, capsules (including jacketed and multi-layered tablets or mixed granules), eye medicaments, mucous membrane adhesives, patches, juices, tinctures, wines, lotions, solutions, essences, suspensions, emulsions, pastes, ointments, creams, gels, special bandage coverings, adhesion dressings, suppositories, medicament sticks, pellets or implantable medicament forms (such as pump fillings) etc. Particular galenical formulations such as liposomes or coated tablets, microemulsions and nanoparticles, including galenical formulations which comprise a particularly rapid or delayed release (depot forms) and combinations thereof are also suitable in particular (R. Voigt, "Pharmazeutische Technologie [Pharmaceutical technology]", 8th edition, Ullstein Mosby Verlag, Berlin 1995; T. Wimmer et al. "Arzneiformen [Medicament forms]" in E. Nürnberg, P. Surmann (editors), Hagers Handbuch der Pharmazeutischen Praxis [Hagers handbook of pharmaceutical practice], volume 2, 5th edition, Springer Verlag, Berlin 1991, 622–1047).

The use of Crataegus plant parts, e.g. in the form of tea, for the preparation of infusions is furthermore possible in the context of the present invention.

In the context of the present invention, the formulations which substantially comprise constituents of Crataegus which are soluble in polar solvents can be employed either as a pharmaceutical preparation (i.e. as a medicament) or as a food supplement.

The invention is described below with the aid of examples.

The actions of various extracts from plants of the species Crataegus on the growth properties and the survival of tumour cells were investigated in the examples described below.

EXAMPLES

Material and Methods

Crataepus formulations

In the context of the present invention, extracts and pressed juices were prepared as Crataegus formulations using the leaves (folii), blossom (flores) and/or fruit (fructus). The following Crataequs species were employed by way of example: Folia cum flore Crataegi according to DAB 10, basic version 1991 "Weißdornblätter mit Blüten [Hawthorn leaves with blossom]": *Crataegus monogyna, Crataegus laevigata* (synonym: *oxyacantha*) and *Crataegus nigra, Crataegus pentagyna* and *Crataegus azarolus;* Fructus Crataegi according to DAC 86, 4th supplement 1992 "Weißdornbeeren [Hawthorn berries]": *Crataegus monogyna, Crataegus laevigata* (synonym: *oxyacantha*) or mixtures thereof, with foreign constituents of not more than 2%, in particular fruit of other Crataegus species (*Crataegus nigra, Crataegus pentagyna* and *Crataegus azarolus*).

The extraction methods varied from maceration via digestion, (exhaustive) percolation to Soxhlet extraction. The particular concentration of the extraction agents and the individual extracted plant (parts) are listed in table 3.

The pressed juices were prepared in accordance with instructions known to the expert (J. Ziegenmeyer, "Zubereitungen auf Pflanzen und Drogen [Formulations of plants and drugs]", loc. cit. and R. Voigt, "Pharmazeutische Technologie [Pharmaceutical technology]", loc. cit.).

The extracts were prepared using the following extraction agents:

water, aqueous ethanol: 45%, 50%, 60%, 70% aqueous methanol: 70% hexane (as a comparison)

Tea infusions were prepared by pouring 150 ml boiling drinking water over in each case 2 g finely cut plant drug. After incubation for 15 minutes, the mixture was sieved through a tea filter. The product was evaporated at 50° C. with application of vacuum, and the resulting dried substance was dissolved in water.

In a further experiment, the extract from Crataegus folium cum flore (i.e. extract prepared from leaves and blossom of Crataegus according to DAB 10 "Weißdornblätter mit Bl üten [Hawthorn leaves with blossom]") prepared with water as the extraction agent and dissolved in water was additionally extracted by shaking with pure hexane in order to remove all the lipophilic constituents which are soluble in hexane. The extraction by shaking was carried out in accordance with the following plan: once with the same volume and then twice with nine times the volume of hexane, so that a reduction of the substances in the aqueous phase which are equally soluble in hexane and water to 1/200 resulted. More lipophilic substances, which dissolve better in hexane than in water, remained in the aqueous phase in a far lower residual concentration than 1/200.

The final concentration sought for the total extract was 200 µg/ml. The Crataegus extracts, which were standardized to flavonoids (hyperoside according to DAB 10, basic edition 1991 "Weißdornblätter mit Blüten [Hawthorn leaves with blossom]" or DAB 10, 2nd supplement 1993 "Weißdornfluidextrakt [Hawthorn fluid extract]" or vitexin or a mixture of vitexin and hyperoside according to NTPP 708/709 "Extrait d'Aubepine" (sec)) or procyanidines (cyanidine chloride according to DAC 86, 4th supplement 1992) as the indicator substance, were dissolved such that the concentration of the indicator substance in the final batch was constant. In the case of flavonoids, this was 4.4 µg/ml, and for procyanidines 2.6 µg/ml. If the indicator substance concentration in the dried extract deviated from 2.2% flavonoids or 1.3% procyanidines, more or less extract was employed accordingly, and the final concentration of the indicator substance remained constant. All the solutions were subjected to sterile filtration through a 0.2 µm syringe filter directly before dilution in the cell culture medium and addition to the cell culture.

The extracts (dried extracts, unless mentioned otherwise) were obtained by various methods described in table 1:

TABLE 1

| Extract | Method | Temperature | Duration |
|---|---|---|---|
| Crataegus folium cum flore | | | |
| Aqueous | exhaustive percolation | 70–80° C. | 20 hours |
| Ethanolic | exhaustive percolation | 40–50° C. | 12 hours |
| Methanolic | exhaustive percolation | 40–50° C. | 12 hours |
| Methanolic | maceration | 15–25° C. | 24 hours |
| Crataegus fructus | | | |
| Ethanolic | exhaustive percolation | 20–30° C. | 8 hours |
| Methanolic | percolation | 50–60° C. | 12 hours |
| Ethanolic fluid extract | exhaustive percolation | 20–30° C. | 8 hours |

For comparison, Crataegus was extracted with hexane as the extraction agent in accordance with the instructions of M. T. Sáenz et al. (loc. cit.). The extract was evaporated at 50° C. in vacuo and then dissolved in 8% Tween® 80 solution (polyoxyethylene sorbitan monooleate).

The dried extracts were standardized to the particular indicator substances mentioned in table 3 by mixing the dried extracts with a varying content of the particular indicator substance or by addition of auxiliaries such as $SiO_2$, maltodextrin, glucose syrup and/or maize starch. These substances had no influence on the growth of the cells investigated or the measurement results in the concentrations employed.

Cell lines

In the context of the present invention, five human tumour cell lines (four carcinoma cell lines, one sarcoma cell line) and one animal carcinoma cell line (cf. tab. 2) were investigated as examples. All the cell lines were kept in permanent cell culture in cell culture bottles with 75 $cm^2$ base area. They were subjected to passage once a week, and the medium was changed twice a week. At the start of the experiment (day 0), the cells were sown in cell culture plates with 96 depressions (96 well plates) in 100 µl medium per well (=0.32 $cm^2$) in each case, with the density shown in table 2. On days 1 and 4, the medium of all the cells was changed, and after the change of medium on day 4, incubation with the active substances (Crataegus formulations, Gentiana, superoxide dismutase, 5-fluorouracil and methotrexate; see below) or the solvents as controls started immediately. The effects of the active substances were measured on day 7 (that is to say after incubation for 72 hours) with two different methods, the so-called MTT assay and the SRB assay (see tab. 2).

thereafter dyeing their protein. This dyeing is then also determined photometrically. Non-living cells are distinguished in that they first detach themselves from the cell culture base and then dissolve in the culture medium. This method therefore also measures only the living cells in a cell culture. The cells growing in 100 µl medium are first fixed with 25 µl 50% cold trichloroacetic acid at 4° C. After incubation for one hour at 4° C., all the non-fixed constituents are removed and those which remain are rinsed five

TABLE 2

| Cell line | Tissue origin/ diagnosis | Pathological classification | Species | Medium | Sowing cells/well | Method |
|---|---|---|---|---|---|---|
| HT-29 | large intestine/ colon carcinoma | carcinoma | human | McCoy's 5A + 10% FCS | 2000 | MTT |
| Caki-1 | kidney/ kidney carcinoma | carcinoma | human | McCoy's 5A + 10% FCS | 3000 | MTT |
| SK-MEL-2 | skin/ malignant melanoma | carcinoma | human | EMEM + NEAA + Napyr CS + 10% FCS | 3000 | SRB |
| U373MG | CNS/ glioblastoma | carcinoma | human | EMEM + NEAA + Napyr + 10% FCS + glutamine | 2000 | SRB |
| SAOS-2 | bone/ osteosarcoma | sarcoma | human | McCoy's 5A + 10% FCS | 7500 | MTT |
| CMT-93 | rectum/rectum carcinonia | carcinoma | animal (mouse) | DMEM + 10% FCS | 3000 | SRB |

Legend to table 2:
EMEM: minimum essential medium, DMEM: Dulbecco's modified Eagle medium, McCoy's 5A: cell culture medium; FCS: foetal calf serum,
NEAA: non-essential amino acids, Napyr: sodium pyruvate; 36 U/ml penicillin and 36 µg/ml streptomycin were added to all the media;
MTT: colorimetric assay for determination of cell enzyine activity (see below), SRB: sulphorhodamine B - assay for determination of the cell protein content (see below); "—": not determined.

MTT assay: The MTT assay (T. Mossman, J. Immunoll. Methods 65 (1983) 55–63) is based on measurement of the metabolic activity of living cells. The substance 3-(4,5-dimethylthiazol-2-yl)-2,5-diphenyltetrazolium bromide (MTT), which the cells reduce intracellularly to the water-insoluble dyestuff formazan, is made available to the cells. This reduction takes place only in metabolically active cells, so that this assay detects exclusively living cells. At the measurement time, in each case 100 µl MTT solution (4 mg/ml PBS, phosphate buffered saline) are added to the cells in 100 µl medium. Incubation for two hours at 37° C. then takes place. Thereafter, the medium is sucked off, so that the dyed living cells adhering to the base of the culture flask remain. These and the dyestuff are dissolved with 100 µl DMSO (dimethylsulphoxide) in the course of 5 minutes, with vigorous shaking. The extinction is then determined photometrically at 570 nm. Its linearity in the range used here, and also its correlation to the number of living cells (counted under the microscope) were detected in preliminary experiments. The particular photometric controls received the same amount of PBS without MTT, instead of the MMT-containing solution. For the evaluation, ΔE was determined by subtraction of the extinction in the controls with PBS from the measurement values with MTT.

SRB assay: The SRB assay (P. Skehan et al., J. Natl. Cancer Inst. 82 (1990) 1107–1112) is based on binding of the dyestuff sulphorhodamine B (SRB) to basic proteins. The principle specifies fixing, with the aid of trichloroacetic acid, the tumour cells adhering to the culture vessel base and times with water. After drying in air, 200 µl 0.4% sulphorhodamine B solution in 1% acetic acid or, in the photometric controls, only acetic acid, are added. After incubation for 30 minutes at room temperature, the dyestuff solution is poured out and the culture is rinsed four times with 1% acetic acid. After removal of the rinsing solution and drying, the dyestuff adhering to the basic proteins is dissolved in 100 µl 10 mM tris-base (tris(hydroxymethyl)aminomethane) in the course of 5 minutes. The extinction was measured at 570 nm or, if the OD (optical density) lay outside the linear range, at 492 nm (for CMT-93 cells). For the evaluation, ΔE was determined by subtraction of the extinction in the controls with acetic acid from the measurement values with SRB.

Results:

The data shown in table 3 are the means of three individual measurements. ΔE measured under the action of the various test substances has additionally been shown in percent of ΔE of the particular solvent controls. The control cells, which received no test substances (Crataegus formulations) but only medium or solvent, reached 100% of their density (number) as defined at the measurement time (day 7). At the time of addition of the test substance (day 4), the cells had already reached approx. 50% of the density, and therefore also 50% of the ΔE to be measured. This means that an inhibition of growth by the test substance which leads to a ΔE measurement value of 50% of the control measurement value denotes that in sum a 100% inhibition of growth (cytostasis) was achieved, and the cell count therefore did not increase further from the time of addition of the test substance. A measurement value of 75% accordingly means an: approx. 50% inhibition of growth during incubation with the test substance. Measurement values which lie below 50% ΔE of the control show that not only has complete cytostasis (inhibition of growth) taken place, but furthermore the cell density has decreased in absolute terms compared with the cell density on addition of the test substance, that is to say in this case the test substance has also induced a cell destruction (cytotoxic effect) in addition to the complete cytostasis.

TABLE 3

|  |  | Cell lines: | | | | | |
| --- | --- | --- | --- | --- | --- | --- | --- |
|  |  | HT-29 | Caki-1 | SAOS-2 | CMT-93 | SKMEL-2 | U373MG |
|  |  | | | Method: | | | |
|  | Solvent (S) | | | MTT Assay | | | SRB Assay |
|  | (final conc) | | | dE mean % control | | | |
| Substance group/ Substance standardized to *Crataegus folium cum flore* | | | | | | | |
| Aqueous extract | H₂O | — | — | — | 0.362 | 0.341 | 0.671 |
| 1.8% vitexin + hyperoside | 0.4% |  |  |  | 102% | 24% | 59% |
| Aqueous extract | DMSO | — | — | — | 0.284 | 1.057 | 0.861 |
| 1.8% vitexin + hyperoside | 0.4% |  |  |  | 83% | 46% | 77% |
| Aqueous extract | propanediol | — | — | — | 0.300 | 0.339 | 0.730 |
| 1.8% vitexin + hyperoside | 0.4% |  |  |  | 102% | 27% | 61% |
| Aqueous extract | EtOH | — | — | — | 0.312 | 0.270 | 0.732 |
| 1.8% vitexin + hyperoside | 0.4% |  |  |  | 85% | 15% | 48% |
| Ethanolic (45%) extract | DMSO | 0.988 | 0.904 | 0.460 | 0.194 | 0.471 | 0.865 |
| 2.37% vitexin | 0.4% | 49% | 67% | 77% | 57% | 21% | 77% |
| Ethanolic (70%) extract | DMSO | 0.975 | 1.046 | 0.568 | 0.222 | 0.793 | 0.322 |
| 2.4% hyperoside | 0.4% | 48% | 77% | 95% | 65% | 35% | 29% |
| Ethanolic (70%) extract | propanediol | 1.104 | 1.061 | 0.619 | 0.254 | 0.392 | 0.373 |
| 2.4% hyperoside | 0.4% | 55% | 77% | 103% | 86% | 31% | 31% |
| Methanolic (70%) extract | DMSO | 2.053 | 0.931 | 0.574 | 0.244 | 0.633 | 0.406 |
| 2% vitexin | 0.4% | 101% | 69% | 96% | 72% | 28% | 36% |
| Methanolic (70%) extract | DMSO | 1.121 | 1.062 | 0.635 | 0.180 | 1.538 | 1.140 |
| 1.41% hyperoside | 0.4% | 55% | 79% | 106% | 53% | 68% | 102% |
| Tea infusion | H₂O | — | — | — | 0.319 | 1.078 | 0.706 |
| dried and dissolved | 0.4% |  |  |  | 90% | 76% | 62% |
| Hexane extract | Tween | 0.117 | 0.141 | 0.039 | 0.176 | 0.402 | 0.143 |
| acc method of Saenz et al. | 0.32% | 120% | 95% | 55% | 73% | 88% | 60% |
| Aqueous extract Ex-hexane | H₂O | — | — | — | 0.374 | 0.889 | 0.533 |
| 1.8% vitexin + hyperoside | 0.4% |  |  |  | 105% | 62% | 47% |
| Ex-hexane after extraction by shaking with 1 × 1 and 2 × 9 volumes hexane (=1/200) Substance group/ Substance standardized for *Crataegus fructus* | | | | | | | |
| Ethanolic (60%) extract | DMSO | 2.223 | 1.221 | 0.652 | 0.324 | 1.689 | 0.634 |
| 1.3% cyanidine chloride | 0.4% | 109% | 90% | 109% | 95% | 75% | 57% |
| Ethanolic (60%) extract | propanediol | 2.474 | 1.292 | 0.607 | 0.372 | 0.903 | 0.742 |
| 1.3% cyanidine chloride | 0.4% | 122% | 94% | 101% | 126% | 72% | 62% |
| Methanolic (70%) extract | DMSO | 2.106 | 1.120 | 0.635 | 0.315 | 1.270 | 0.646 |
| 1.4% cyanidine chloride | 0.4% | 104% | 83% | 106% | 92% | 56% | 58% |
| Ethanolic (50%) | EtOH | 1.024 | 0.181 | 0.237 | — | 1.935 | 1.596 |
| fluid extract (4 mg/ml) | 0.09% | 54% | 12% | 40% |  | 109% | 105% |
| Pressed juice 10 mg/ml | H₂O | 0.574 | 0.065 | 0.134 | — | 1.270 | 0.971 |
|  | 1% | 30% | 4% | 23% |  | 89% | 85% |
| Substance group/ Substance standardized for Superoxide scavenger | | | | | | | |
| *Gentiana lutea radix* | H₂O | 1.699 | 1.435 | 0.532 | 0.314 | — | — |
| 200 μg/ml aqueous | 0.4% | 89% | 97% | 93% | 88% |  |  |
| (dried) extract 100° C. - 2h - 100 g/l | | | | | | | |
| Superoxide dismutase | H₂O | 1.725 | 1.442 | 0.564 | 0.326 | 1.340 | — |
| 1 μg/ml | 0.10% | 90% | 97% | 98% | 92% | 94% |  |
| From bovine erythrocytes Positive controls cytostatics | | | | | | | |
| 5-Fluorouracil | medium | 0.973 | — | — | 0.191 | — | — |
| 25 μg/ml |  | 53% |  |  | 63% |  |  |
| Methotrexate | medium | — | 0.679 | 0.259 | — | 2.429 | 1.449 |
| 45 μg/ml |  |  | 47% | 41% |  | 119% | 135% |
| Solvent controls |  | 1.824 | 1.447 | 0.626 | 0.304 | 2.035 | 1.075 |
| Medium | | | | | | | |
| Tween 80 |  | 0.097 | 0.148 | 0.070 | 0.240 | 0.455 | 0.237 |

TABLE 3-continued

| | | Cell lines: | | | | | |
|---|---|---|---|---|---|---|---|
| | | HT-29 | Caki-1 | SAOS-2 | CMT-93 | SKMEL-2 | U373MG |
| | | | | Method: | | | |
| | Solvent (S) | MTT Assay | | | | SRB Assay | |
| | (final conc) | dE mean % control | | | | | |
| (aq. hexane extract) 0.32% | | 5% | 10% | 11% | 79% | 22% | 22% |
| Propanediol 0.40% | | 2.019 / 111% | 1.380 / 95% | 0.601 / 96% | 0.295 / 97% | 1.251 / 62% | 1.189 / 111% |
| DMSO 0.40% | | 2.031 / 111% | 1.352 / 93% | 0.600 / 96% | 0.342 / 112% | 2.278 / 112% | 1.119 / 104% |
| Ethanol 0.4% | | 1.909 / 105% | 1.470 / 102% | 0.590 / 94% | 0.368 / 121% | 1.780 / 87% | 1.523 / 142% |
| H$_2$O 0.4% | | 1.916 / 105% | 1.481 / 102% | 0.575 / 92% | 0.356 / 117% | 1.428 / 70% | 1.142 / 106% |

"—" not determined

Unless mentioned otherwise, all the extracts listed in table 3 are dried extracts which were dissolved in the particular solvent stated. The final solvent concentration stated (final conc.) was present in the test batch, that is to say in the cell medium. The results of all the control conditions are shown at the end of table 3.

Aqueous dried extract from Crataegus leaves and blossom showed a significant cytostatic/cytotoxic action on SKMEL-2 and U373MG cells. This action was very largely independent of what the dried extract was dissolved in (water, DMSO, 1,2-propanediol or ethanol). The solvents themselves had no substantial intrinsic effect on cell growth.

Crataegus extract which had been prepared with 45% aqueous ethanol also showed a cytostatic/cytotoxic action on SKMEL-2 and U373MG cells, and in particular on the HT-29 and Caki-1 cells additionally investigated and on CMT-93 cells. An inhibition of the growth of osteosarcoma cells. SAOS-2 was additionally also achieved. Crataegus extracts which had been obtained with 70% aqueous ethanol and had been dissolved in DMSO after removal of the extraction agent showed an action profile identical to that of the extract prepared with 45% ethanol as the extraction agent, with the exception of the weaker action on the osteosarcoma cells. Here also, the solvent (DMSO or 1,2-propanediol) had no influence on the action of the extract.

Crataegus extract which had been prepared with 70% methanol as the extraction agent and standardized to 2% vitexin also showed a cytostatic/cytotoxic activity on Caki-1, CMT-93, SKMEL-2 and U373MG cells. The action profile was therefore very similar to that of the ethanolic extract. Methanolic extract: standardized to 1.41% hyperoside showed a similar action profile. It additionally inhibited the growth of HT-29 cells, but not that of U373MG cells.

Tea infusion is another of the possible preparation routes of an aqueous extract. Interestingly, the results were the same in respect of the action profile of tea infusion and aqueous extract.

In the context of the present invention, in addition to the Crataegus formulations which substantially comprise constituents of Crataegus which dissolve in polar solvents, formulations from Crataegus which were obtained with hexane as the extraction agent and substantially comprise triterpene compounds (M. T. Sáenz et al., loc. cit.) were also investigated for comparison.

Hexane extract from Crataegus dissolved in 8% Tween® 80, and in the test batch the final concentration of 0.32% Tween® 80 could be achieved. This was therefore lower by more than a factor of 2 than described by the authors (M. T. Sáenz et al., loc. cit.). Nevertheless, this solvent concentration led to a massive damage to the cells, with dying off to 5 to 22% of the control cell count (exception: CMT-93 cells). It is therefore to be assumed that the remaining cells were also severely predamaged by the solvent.

The action spectrum of the purely lipophilic hexane extract differed clearly from that of the extracts from Crataegus used according to the invention. The hexane extract had virtually no action on Caki-1, HT-29 and SIMEL-2 cells, while in contrast the Crataegus formulations employed according to the invention had a cytostatic/cytotoxic action on these, which was even particularly potent on the last two cells mentioned. The pharmaceutical profile of the formulations which substantially comprise constituents of Crataegus which are soluble in polar solvents thus differs significantly from that of the lipophillic triterpene compounds obtained from Crataegus.

To check these results, a further comparative experiment was carried out. In this, aqueous dried extract was dissolved in water and then extracted by shaking with pure hexane. Substances which are just as readily soluble in water as in hexane were reduced to 1/200 of their original concentration in the aqueous phase in this manner. The concentrations of more lipophilic substances, i.e. substances which dissolve better in hexane than in water, were reduced still considerably further, however, by the additional extraction by shaking against hexane (see above).

Interestingly, the aqueous extract also showed the same action profile after extraction by shaking with hexane as before, including the inhibition of the SKMEL-2 and U373MG cells. The effect on SKMEL-2 cells here was reduced only minimally. The action of the aqueous extract was not reduced at all in respect of the U373MG cells.

In further comparative experiments, superoxide scavengers such as gentian extracts (Gentiana lutea radix, extracted with 100 g/l water at 100° C. over 2 hours; cf. JP-A 4-5237) and superoxide dismutase from bovine erythrocytes (JP-A 4-5237) were employed, which provably had no cytostatic or cytotoxic effects on the cell lines investigated (cf. table 3).

Extracts and pressed juice from Crataegus fruit (Crataegus fructus) were furthermore investigated, the extracts having been prepared with 50% or 60% ethanol or 70% methanol as the extraction agent. The action profile of the dried extracts which had been prepared by extraction with 60% ethanol or 70% methanol, with inhibition of the growth of SKMEL-2 and U373MG cells, was comparable. The pressed juice additionally investigated, like the ethanolic fluid extract investigated, showed a growth-inhibiting action on HT-29, Caki-1 and SAOS-2 cells.

Chemically defined cytostatics were furthermore investigated as positive controls. In each case a cytostatic which is described as effective for the particular diagnosis in clinical pharmacology was employed per cell lines. On four of the six cell lines investigated, the cytostatics showed an inhibiting action. On the other hand, the malignant melanoma and glioblastoma cells showed resistance to methotrexate in the concentration employed.

The present examples therefore demonstrate the suitability of the formulations which substantially comprise constituents of Crataegus which dissolve in polar solvents for the prophylaxis and/or treatment of tumour diseases. In particular, the Crataegus formulations used according to the invention show a broad action spectrum on various tumour cell types and an action which is comparable to or even better than that of customary cytostatics/cytotoxics, the Crataegus formulations having no side effects.

What is claimed is:

1. A method of treatment of a tumor disease comprising administering a composition comprising a formulation from Crataegus in a pharmaceutically acceptable carrier to a person in need of said treatment, wherein said formulation comprises constituents of Crataegus which are soluble in a polar solvent.

2. A method of claim 1, wherein said formulation is prepared from leaves, blossom or fruit of Crataegus or mixtures thereof.

3. A method of claim 1, wherein said formulation is obtainable by maceration, digestion, percolation or other extraction.

4. A method of claim 1, wherein said formulation is a pressed juice.

5. A method of claim 4, wherein said pressed juice is prepared from Crataegus fruit.

6. A method of claim 1, wherein said formulation is an extract.

7. A method of claim 6, wherein said extract is obtainable by extraction with at least one component selected from the group consisting of water, alcohol, acetic acid, liqueur wine, a supercritical gas, and a supercritical liquid as an extraction agent.

8. A method of claim 7, wherein said extraction agent is at least one alcohol selected from the group consisting of methanol, ethanol, propanol, butanol, pentanol and hexanol.

9. A method of claim 7, wherein said extraction agent is a mixture of alcohol and water with a content of 10 to 99 vol. % alcohol.

10. A method of claim 2, wherein said extraction agent is a mixture of alcohol and water with a content of 15 to 95 vol. % alcohol.

11. A method of claim 1, wherein said formulation is obtainable from Crataegus plant parts which have been subjected to an extraction with an apolar extraction agent before the preparation of the formulation.

12. A method of claim 1, wherein said formulation is a dried extract which is obtainable by removal of the extraction agent or solvent and subsequent drying.

13. A method of claim 12, wherein said dried extract is subsequently dissolved, emulsified, dispersed or suspended in a liquid.

14. A method of claim 13, wherein said liquid is at least one component selected from the group consisting of water, an aqueous salt solution, ethanol, a syrup and a wine.

15. A method of claim 1, wherein said formulation comprises at least one of about 0.1 to 13 wt. % flavonoids and/or about 0.05 to 20 wt. % procyanidines.

16. A method of claim 1, wherein said tumor disease is at least one disease selected from the group consisting of a malignant disease and a semi-malignant neoplastic disease.

17. A method of claim 1, wherein said formulation is an infusion of at least one plant part of Crataegus.

18. A method of claim 8 wherein said alcohol is selected from the group consisting of methanol, ethanol, propanol, butanol, pentanol, hexanol, isomers of any one of these and mixtures of any two of said alcohols.

19. A composition for treatment of a tumor disease comprising a formulation from Crataegus in a carrier, wherein said formulation comprises constituents of Crataegus which are soluble in a polar solvent.

20. A composition of claim 19, wherein said carrier is a pharmaceutical carrier.

21. A composition of claim 19, wherein said composition is a food supplement.

22. A method of preparing an infusion of at least one plant part of Crataegus for the prophylaxis or treatment of a tumor disease comprising mixing said plant part with a solvent.

* * * * *